United States Patent [19]
Rainin et al.

[11] 4,079,976
[45] Mar. 21, 1978

[54] SOFT CONTACT LENS MANIPULATION DEVICE

[75] Inventors: Edgar A. Rainin, 5747 Tamarack Way, Concord, Calif. 94521; Joseph F. Pimentel, Antioch, Calif.

[73] Assignee: Edgar A. Rainin, Concord, Calif.

[21] Appl. No.: 731,576

[22] Filed: Oct. 12, 1976

[51] Int. Cl.² .................................................. A61F 9/00
[52] U.S. Cl. .................................. 294/1 CA; 294/64 R
[58] Field of Search .................... 294/1 CA, 64 R; 128/303 R; 206/5.1; 351/160

[56] References Cited

U.S. PATENT DOCUMENTS

| 2,919,696 | 1/1960 | Rinaldy | 294/1 CA UX |
| 3,139,298 | 6/1964 | Grabiel | 294/1 CA |
| 3,304,113 | 2/1967 | Hutchison | 294/1 CA X |
| 3,424,486 | 1/1969 | Corley | 294/1 CA UX |
| 3,879,076 | 4/1975 | Barnett | 294/1 CA |

FOREIGN PATENT DOCUMENTS

| 1,401,116 | 12/1965 | France | 294/1 CA |

Primary Examiner—Johnny D. Cherry
Attorney, Agent, or Firm—Theodore J. Bielen, Jr.; David B. Harrison

[57] ABSTRACT

A device for placing and removing of a soft contact lens from the eye utilizing a tip for presenting one side of a soft contact lens in a shape configuration to allow placement on the eye. The tip holds the soft contact lens against the pull of gravity, but releases the lens when the other side of the lens contacts the eye, producing a surface tension. A handle connects to the tip permitting the hand to manipulate the tip and the lens thereupon.

14 Claims, 7 Drawing Figures

SOFT CONTACT LENS MANIPULATION DEVICE

BACKGROUND OF THE INVENTION

The present invention relates to a novel soft contact lens device used for the insertion and removal of the same.

Contact lenses can be made to correct most visual conditions correctable by regular eyeglasses. Moreover, contact lenses are not readily visible and provide the user with a wider field of vision than eyeglasses do. Participation in active sports does not prevent the use of contact lenses since they do not easily break.

The first contact lenses were of the "hard" variety, that is to say, they are molded of a relatively rigid material, usually methylmethacrylate, and formed by heat and pressure to the exact shape of the wearer's eye. The user must learn to wear them over a period of time. Many persons have experienced difficulty in wearing hard contact lenses.

A recent innovation has been the "soft" contact lens constructed of flexible and liquid absorbent material such as 2-hydroxyethyl methacrylate. Although very comfortable to wear, the soft contact lens encounters a number of problems, including the difficulty of insertion and removal, especially in elderly persons, and susceptibility to contamination. A device to minimize touching of the soft contact lens with the human hand and assist in its insertion and removal is needed.

SUMMARY OF THE INVENTION

In accordance with the present invention a novel device for the manipulation of soft contact lenses is provided. The device utilizes tip means for holding a soft contact lens against the normal pull of gravity for transportation and placement of the same. The tip means touches one side of a soft contact lens and maintains it in a shape, or configuration which will allow placement of the lens on the eye. Contact between the outer surface of the eye and the soft contact lens will create an adhesive force which overcomes the holding force between the tip means and the other side of the soft contact lens. The tip means may be constructed of soft and pliable material having an elastic memory to obviate the possibility of damage to the eye during use.

Connected to the tip means is a handle means for grasping by the hand. The tip means and handle means may be integral with one another. The handle means may possess a relative degree of rigidity compared to the tip means, such that alignment of the lens with the eye is easily and repeatedly accomplished.

The end of the handle means may connect to a stand which supports the tip means and handle means in a disposition away from the supporting surface of the stand, thus further eliminating the possibility of contamination of the lens by a non-sterile environment. Again, the tip means, handle means, and stand may be constructed as one piece.

Where the tip means is a tube, the first edge portion of the tube contacts one side of the contact lens ie: the convex side of the lens. The other edge portion of the tube may substantially circumscribe the handle means with the handle means and the tube's other edge portions having a contrasting appearance. Further, this contrast may form an optical target which indicates the position of the axis of the tube, thus guiding the user in lens placement by denoting the proper orientation of the soft contact lens in relation to the eye surface.

The tube may externalize in an elastomeric type material being soft and having an elastic memory. By contrast the handle means may possess a greater degree of rigidity than the elastomeric tip. In this respect, the edge of the tip means contacts the soft contact lens. It has been found that certain ranges of edge surface areas and sizes of the tip means enhance the invention's workability, as will be detailed as the specification continues.

Also, a suction means may be included for reinforcing the adhesion force exerted in the holding of the convex side of the soft contact lens by the tip means. In this manner, the adhesive force between the outer surface of the eye and the concave portion of the soft contact lens is overcome and the lens removed.

Along these lines, it may be seen that finger and hand contact with the soft contact lens has been minimized — if not eliminated —, by the application of the present invention. This aspect of the device is particularly useful when the soft contact lens is to be inspected for dirt, lint, and other like non-hygienic elements. Also, the device simplifies soft contact lens insertion and removal by doctors, nurses, and other persons administering care to wearer of soft contact lenses. Inexperienced or handicapped users require the present device to manipulate these lenses.

With respect to the foregoing it is therefore an object of the present invention to provide a soft contact lens manipulation device which will effectively and quickly aid in the removal and insertion of a soft contact lens.

It is another object of the present invention to provide a soft contact lens manipulation device which minimizes and/or eliminates the touching of a soft contact lens by the human hand.

It is still another object of the present invention to provide a soft contact lens manipulation device which permits inspection and cleaning of exposed surfaces of such a lens without touching the same to achieve a clean and useable lens.

It is yet another object of the present invention to provide a soft contact lens manipulation device which will greatly help one person to insert and remove lenses from another person.

Yet another object of the present invention is to provide a soft contact lens manipulation device which will assist handicapped persons therewith.

Another object of the present invention is to provide a soft contact lens manipulation device which can itself be readily sterilized and stored for instant retrieval and use.

The invention possesses other objects and advantages especially as concerns particular features and characteristics thereof which will become apparent as the specification continues.

Various aspects of the present invention will evolve from the following detailed description of the preferred embodiments thereof which should be taken in conjunction with the accompanying drawings.

DESCRIPTION OF THE PREFERRED EMBODIMENTS

Figure 1:
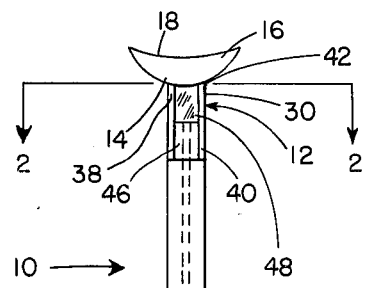
FIG. 1 is a side view of the invention with the inclusion of a suction means.

The invention as a whole is shown in the drawings by reference character 10 and includes as one of its elements a tip means 12 intended for holding the convex side 14 of a soft contact lens 16, FIG. 1. Tip means 12 may be constructed of soft material having an elastic memory such as silicone rubber, polyvinyl chloride, and the like. In this manner damage to the eye is eliminated during maneuvering of lens 16. Lens 16 may be of any type such as the SOFLENS manufactured by Bausch & Lomb, Rochester, New York. Generally, the soft contact lens is constructed of a water absorbing polymer material such as 2-hydroxyethyl methacrylate. The radius of curvature of such a lens is usually between 8.0 millimeters and about 10 millimeters, however, the soft contact lens is quite flexible to the point of being gelatinous. The trend has been to design thinner soft contact lenses to obtain greater comfort, but thinner lenses are more flexible and more difficult to handle. The present invention is useable with the thinnest known soft contact lens.

Figure 4:
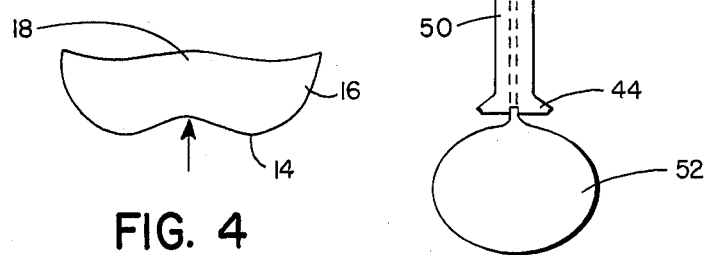
FIG. 4 is a schematic view of a typical force on a soft contact lens, with arrows depicting such a force.

Tip means 12 holds lens 16 by the force of adhesion due to the surface tension imparted by the liquid absorbed within lens 16. Such an adhesive force on the convex side 14 of lens 16 will support the same against the normal pull of gravity. Also tip means 12 will support lens 16 in a configuration such that concave side 18 will conveniently place on the cornea and sclera of eye 20. Turning to FIG. 4, an improper force on lens 16 will buckle the convex side 14 and distort, somewhat, the concave side 18 causing difficulty in the placement of the lens 16. FIG. 4 represents the effect of a force on the central area of convex side 14, which would parallel the use of a finger to support lens 16 by resting the convex side 14 on such a finger. This effect is especially characteristic of a thin soft contact lens.

Figure 7:
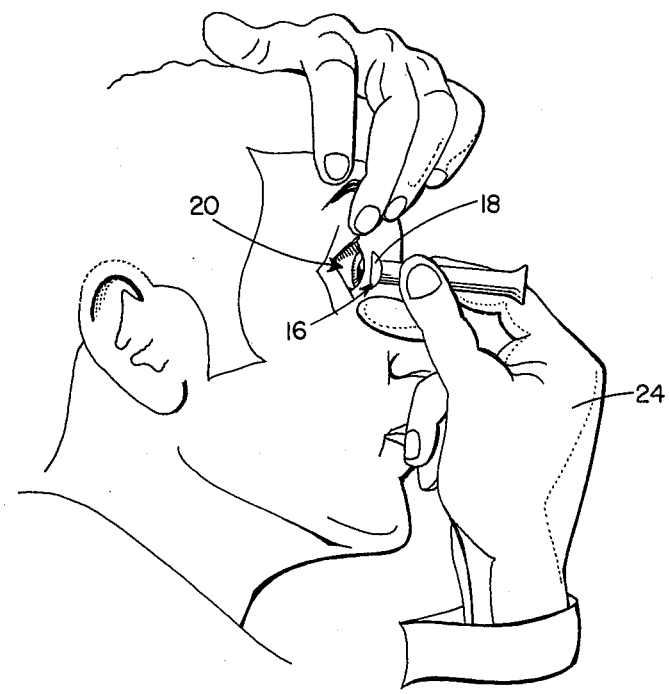
FIG. 7 is a side view showing the soft contact lens insertion technique using the device of the present invention.

Connected to tip means 12 is handle means 22 which may possess a greater amount of stiffness or rigidity than tip means 12. It has been found that the combination of a rigid handle means and soft and elastic tip means provides superior control in the placement of lens 14, FIG. 7. The handle is grasped by the hand 24 of the individual user or other person performing the manipulation. The adhesive force between eye 20 and convex side 18 of lens 16 overcomes the adhesive force between tip means 12 and convex side 14 of lens 16. The tip means 12 and handle means 22 preferably are constructed of material which is resistant to heat sterilization in an autoclave or steam jacket.

Figures 5, 6:
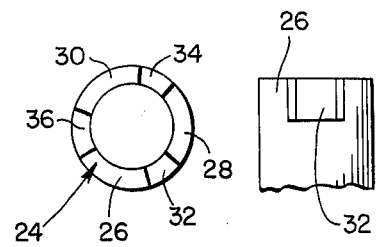
FIG. 5 is a top plan view of an alternate embodiment of the tip means.
FIG. 6 is a broken side view of an alternate embodiment of the tip means.

The preferred embodiment FIGS. 1, 2, 3 and 7 depicts tip means 12 as a tube of round cross-sectional configuration, but it is deemed equivalent to construct tip means in a variety of shapes. For example, tip means 12 may be polygonal or non-continuous, as illustrated in FIGS. 5 and 6, where a tripod 24 having supports 26, 28, and 30 and interposed slots 32, 34, and 36 form a discontinuous ring with the upper surfaces of supports 26, 28 and 30 intended to contact sides 14 of lens 16.

FIG. 1 shows tip means 12 as a tube having a first edge portion 38 including edge 42, which curves to the radius of curvature of lens 16, and touches or contacts convex side 14 of lens 16. As will be discussed, the side of tip means 12 depends on the area of contact thereof with lens 16. Curved edge 42 permits better contact with lens 16 without distortion of concave side 18.

The handle means 22 may be connected to stand 44 which may be manufactured as a separate piece or as integral with handle means 22, FIG. 1. Stand 44 may rest on a surface, serving to retain lens 16 in a position remote from association with a non-sterile environment. Also, the lens 16 may be inspected and cleaned while held to device 10 upheld by stand 44.

Tip means 12 in the form of a tube fits over the end portion 46 of handle means 22, thus second edge portion 40 substantially surrounds handle means 22 creating chamber 48. Aperture 50 extends from chamber 48 to the end of stand 44. Suction means 52, such as an elastomeric ball, would reinforce the holding of lens 16 by tip means 12, after squeezing the same.

Figure 2:
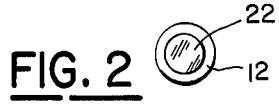
FIG. 2 is a view taken along line 2—2 of FIG. 1.
Figure 3:
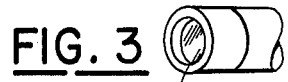
FIG. 3 is a slightly rotated perspective view of the item shown in FIG. 2.

Handle means 22 may contrast in appearance to tube 12, FIGS. 2 and 3. As described, handle means 22 is an opaque object while tube 12 is transparent or translucent. The centered handle means 22 and tube 12 would appear as concentric circles when the axis of tube 12 is coincident with the optical axis of eye 20. Such an event would indicate proper alignment of lens 16 on the edge of tip means 12 for placement of lens 16 on eye 20. If the alignment of the tube 12 axis is not correct the opaque handle means 22 would appear elliptical to the user. As can be surmised, an optical target 54 exists, visible through transparent lens 16 which guides this lens onto the eye 20.

The following table exemplifies the values of round tube sizes useable as tip means 12 for soft contact lenses.

TABLE "A"

1. Maximum outside diameter of TUBE 13 millimeters
2. Minimum outside diameter of TUBE 3 millimeters
3. Maximum wall thickness of TUBE 3.2 millimeters
4. Minimum wall thickness of TUBE 0.4 millimeters For any configuration of tip means 12 the surface area intended to contact convex side 14 of lens 16 will range from 3 square millimeters to 100 square millimeters, for all known soft contact lens designs. A preferred range of between 7 and 50 square millimeters is useable with soft contact lenses most often worn by humans.

In operation, the user of device 10 grasps handle means 22 and directs tip means 12 to the convex side 14 of soft contact lens 16. The adhesive force therebetween will support lens 16 on device 10 against the pull of gravity. The user then inspects the lens 16 for visible contaminants such as dust, dirt, lint and the like and may employ both hands to prepare such a cleaning operation by placing stand 44 on a flat surface. After inspection of lens 16, it is inserted on the eye 20 with the help of optical target 54, if the user and person inserting are identical entities. The device is withdrawn from the surface area of eye 20 and lens 16 remains thereon for use.

When removing lens 16, the user squeezes suction means 52 and aligns the tip means 12 with the eye 20, using optical target 54. Edge 42 touches convex side 14 of lens 16 and the suction means is released. The adhesive force between convex side 14 and edge 42 and suction force exerted by suction means 52 will overcome the force of adhesion between eye 20 and concave side 18 of lens 16, thus leaving lens 16 on tip means 12.

While in the foregoing specification embodiments of the invention have been set forth in considerable detail for purposes of making a complete disclosure of the invention, it will be apparent to those skilled in the art that numerous changes may be made in such details without departing from the spirit and principles of the invention.

What is claimed is:

1. A device intended for aiding the placement and removing of a soft contact lens in the eyes comprising:
    a. tip means for holding one side of a soft contact lens in a shape configuration intended for placement on the eye, said tip means adapted for holding the soft contact lens against the normal pull of gravity and releasing the soft contact lens upon exertion of adhesive force between the eye and the other side of the soft contact lens; said tip means having an axis intended for intersecting the one side of the soft contact lens;
    b. handle means for grasping by the hand, said handle means connected to said tip means, said handle means having a reduced end portion contrasting in appearance to said tip means; said tip means substantially surrounding said handle means reduced end portion to form an optical target indicating the position of said axis of said tip means.

2. The device of claim 1 in which said tip means is a tube having first and second edge portions, said tube's first edge portion contacting the soft contact lens and said tube's second edge portion substantially surrounding said handle means reduced end portion.

3. The device of claim 2 in which said tube is soft and has an elastic memory and said handle means possesses relatively more rigidity than said tip means.

4. The device of claim 2 in which said tube is a substantially round tube and has an outside diameter ranging between three millimeters and thirteen millimeters and a wall thickness having an average range between 0.4 millimeters and 3.2 millimeters.

5. The device of claim 4 in which said tube's first edge portion has an edge including a surface contacting the soft contact lens, said edge surface curved to substantially the radius of curvature of the soft contact lens.

6. The device of claim 2 in which said tip means has a surface area intended to contact one side of a soft contact lens ranging from three square millimeters to 100 square millimeters.

7. The device of claim 6 in which said tip means has a surface area intended to contact one side of a soft contact lens ranging from 7 square millimeters to 50 square millimeters.

8. The device of claim 7 in which said tube is soft and has an elastic memory and said handle means possesses relatively more rigidity than said tip means.

9. The device of claim 1 which additionally comprises a stand connected to said connected tip means and handle means.

10. The device of claim 9 which additionally includes suction means for reinforcing the holding by said tip means of one side of a soft contact lens.

11. The device of claim 1 in which said tip means has a surface area intended to contact one side of a soft contact lens ranging from 3 square millimeters to 100 square millimeters.

12. The device of claim 11 in which said tip means has a surface area intended to contact one side of a soft contact lens ranging from 7 square millimeters to 50 square millimeters.

13. The device of claim 1 which additionally comprises a stand connected to said connected tip means and handle means.

14. The device of claim 13 which additionally includes suction means for reinforcing the holding by said tip means of one side of a soft contact lens.

* * * * *